United States Patent [19]

Large et al.

[11] 4,152,372
[45] May 1, 1979

[54] THIONOPHOSPHATES

[75] Inventors: George B. Large, Orinda, Calif.; Leland S. Pitt, Greenville, Miss.

[73] Assignee: Stauffer Chemical Company, Westport, Conn.

[21] Appl. No.: 897,319

[22] Filed: Apr. 18, 1978

Related U.S. Application Data

[62] Division of Ser. No. 643,969, Dec. 24, 1975, Pat. No. 4,123,526.

[51] Int. Cl.$^2$ ............................................ C07F 9/165
[52] U.S. Cl. ................................................. 260/940
[58] Field of Search ........................................ 260/940

[56] References Cited

U.S. PATENT DOCUMENTS 3,299,188  1/1967  Schicke .............................. 260/940

Primary Examiner—Anton H. Sutto
Attorney, Agent, or Firm—M. Henry Heines

[57] ABSTRACT

Compounds which are useful as insecticide activators are described herein. The compounds are defined by the following formula:

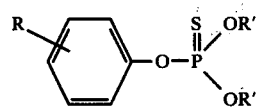

wherein R is selected from the group consisting of lower alkoxy, dimethyl, trimethyl, halogen, dihalogen, trifluoromethyl, acetyl, acetamido, carbomethoxy, carbethoxy, methylenedioxy and

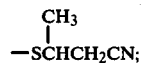

and R' is methyl or ethyl.

1 Claim, No Drawings

THIONOPHOSPHATES

This is a division of application Ser. No. 643,969, filed Dec. 24, 1975, now U.S. Pat. No. 4,123,526.

BACKGROUND OF THE INVENTION

Among the many insecticidal compounds, the phthalimidothiophosphates have reached a relatively high degree of commercial success. These compounds are toxic to a large number of insect pests at concentrations varying with the resistance of the insect. Some of these compounds are described in U.S. Pat. No. 2,767,194, specifically N-(mercaptomethyl) phthalimide S-(O,O-dimethylphosphorodithioate). The endeavor to extend the usefulness of the thiophosphates by increasing their effectiveness and lowering their cost has led to extensive studies on another class of biologically active chemicals, customarily referred to as activators.

DETAILED DESCRIPTION OF THE INVENTION

It has been discovered that the activity of insecticidally active thiophosphate compounds can be enhanced by using an activator having the formula

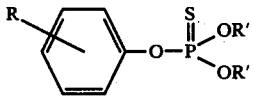

wherein R is selected from the group consisting of lower alkoxy, dimethyl, trimethyl, halogen, dihalogen, trifluoromethyl, acetyl, acetamido, carbomethoxy, carbethoxy, methylenedioxy, and

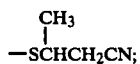

and R' is methyl or ethyl. By "lower alkoxy" is meant methoxy or ethoxy.

The activator compound is manufactured by reacting the properly selected substituted phenol with a strong base to form the phenoxide. The phenoxide is subsequently reacted with the O,O-disubstituted-chloridophosphorothioate to form the desired product. The raw materials described above are commercially available compounds. The reaction takes place in the presence of inert non-reactive solvents. The end product is isolated, purified, and admixed with the insecticidal thiophosphate compound. The amount of activator admixed therewith can range from about 1:0.1 to about 1:10 parts insecticidal compound to activator compound. The insecticide-activator mixture is applied to the habitat of the insect in a conventional manner.

In order to illustrate the merits of the present invention, the following examples are provided:

EXAMPLE 1

O,O-Dimethyl-O-(3-acetamidophenyl) Phosphorothioate

Two point five (2.5) g (0.06 mole) of powdered sodium hydroxide was added to a solution of 7.6 g (0.05 mole) of 3-acetamidophenol in 100 ml of tetrahydrofuran, with continuous stirring. The solution was stirred for an additional 15 minutes. Then 8.0 g (0.05 mole) of O,O-dimethylchloridophosphorothioate was added and stirred for one hour at room temperature. The mixture was diluted with an equal volume of benzene and washed with water. The organic phase was then dried over anhydrous magnesium sulfate. The solvent was stripped in vacuo to yield 9.8 g (71% yield) of product, identified by NMR and infrared spectroscopy analyses as O,O-dimethyl-O-(3-acetamidophenyl) phosphorothioate, $n_D^{30}$ 1.5525.

EXAMPLE II

O,O-Diethyl-O-(3-acetamidophenyl) Phosphorothioate

The procedure of Example I was followed, using 2.5 g (0.06 mole) of powdered sodium hydroxide, 7.6 g (0.05 mole) of 3-acetamidophenol, and 9.45 g (0.05 mole) of O,O-diethylchloridophosphorothioate. The product yield was 12.0 g (79% yield), identified by NMR and infrared spectroscopy as O,O-diethyl-O-(3-acetamidophenyl) phosphorothioate, $n_D^{30}$ 1.5291.

Additional compounds were synthesized in a similar manner using appropriate starting materials. These compounds are listed in the following table.

TABLE I

| | R | R' | $n_D^{30}$ |
|---|---|---|---|
| Example 3 | CH$_3$<br>2-SCHCH$_2$C≡N | C$_2$H$_5$ | 1.5379 |
| Example 4 | 3-OC$_2$H$_5$ | C$_2$H$_5$ | 1.5139 |
| Example 5 | 3,5-CH$_3$ | C$_2$H$_5$ | 1.5076 |
| Example 6 | 4-CCH$_3$ (O) | C$_2$H$_5$ | 1.5229 |
| Example 7 | 3,4-CH$_3$ | C$_2$H$_5$ | 1.5118 |
| Example 8 | 2,3-CH$_3$ | C$_2$H$_5$ | 1.5137 |
| Example 9 | 3,4-methylenedioxy | C$_2$H$_5$ | 1.5244 |
| Example 10 | 2,3-Cl | C$_2$H$_5$ | 1.5333 |
| Example 11 | 3,5-Cl | C$_2$H$_5$ | 1.5271 |
| Example 12 | 3,4,5-CH$_3$ | C$_2$H$_5$ | 1.5159 |
| Example 13 | 2,3,5-CH$_3$ | C$_2$H$_5$ | 1.5114 |
| Example 14 | 3-CF$_3$ | C$_2$H$_5$ | 1.4668 |
| Example 15 | 3-COCH$_3$ (O) | C$_2$H$_5$ | 1.5134 |
| Example 16 | 3-COC$_2$H$_5$ (O) | C$_2$H$_5$ | 1.5069 |
| Example 17 | 3-Cl | C$_2$H$_5$ | 1.5177 |
| Example 18 | 3-Br | C$_2$H$_5$ | 1.5336 |

INSECTICIDAL EVALUATION

A. Salt-marsh Caterpillar [*Estigmene acrea* (Drury)]

Test solutions are prepared by dissolving equal aliquots of the toxicant and activator in a 50-50 acetone-water solution. Sections of curly dock [*Rumex crispus* (L.)] leaves, 1–1.5 inches in length are immersed in the test solutions for 1 to 2 seconds and placed on a wire screen to dry. The dried leaf is placed on a moistened piece of filter paper in a Petri dish and infested with five third-instar larvae. Test concentrations for both toxicant and activator range from 0.05% down to that at which 50% mortality occurs. Mortality of the larvae is recorded after 48 hours and the LD$_{50}$ values are expressed as percent toxicant in the acetone-water solutions.

B. Tobacco Budworm [*Heliothis virescens* (F.)]

The procedure is the same as that used for the Salt-marsh Caterpillar, except that leaves of Romaine lettuce [*Latuca sativa*] are utilized as the host plant rather than curly dock. Test concentrations range from 0.1% downward.

C. Cabbage Looper [*Trichoplusia ni*]

The procedure is the same as that used for the Salt-marsh Caterpillar, except that cotyledons of squash [*Curcurbita pepo*] are utilized as the host plant rather than curly dock. Test concentrations range from 0.1% downward.

D. Black Bean Aphid [*Aphis fabae* (Scop.)]

Test solutions are prepared by dissolving equal aliquots of the toxicant and activator in a 50-50 acetone-water solution. Nasturtium plants (*Tropaeolum sp.*), approximately 5 cm tall, are transplanted into sandy loam soil in 3 inch clay pots and infested with 25-50 black bean aphids of mixed ages. Twenty-four hours later the plants are sprayed, to the point of runoff, with the test solutions. Treated plants are held in the greenhouse and mortality is recorded after 2 days. Test concentrations range from 0.05% down to that at which 50% mortality occurs.

E. German Cockroach [*Blatella germanica* (Linné)]

Equal aliquots of toxicant and activator are diluted in a 50-50 acetone-water solution. Two cc of the solutions are sprayed through a DeVilbiss type EGA hand spray gun into circular cardboard cages containing 10 one-month old German cockroach nymphs. The test cages are covered on the bottom with cellophane and the top with tulle netting. Percent mortality is recorded two days later. Test concentrations range from 0.1% down to that at which 50% mortality occurs. All $LD_{50}$ values are expressed as percent toxicant.

Activating Factor

The activating factor (A.F.) is computed by the following formula:

$$A.F. = \frac{LD_{50} \text{ of Toxicant} \cdot \frac{1}{XY+1}}{\text{Experimental } LD_{50} \text{ of Combination}}$$

where  X = the weight ratio of activator to toxicant, and
Y = the ratio of the $LD_{50}$ of the toxicant to the $LD_{50}$ of the activator.

The experimental $LD_{50}$ of the combination is in terms of the toxicant only.

The activating factor is therefore the expected $LD_{50}$ of the combination divided by the experimental $LD_{50}$. It is noted that when the observed response is greater than the expected, the activating factor is greater than one. When this result is observed, the toxicant has been activated The results of the evaluation tests described above are set forth in the following table.

TABLE II
CONTACT ACTIVITY: APPROXIMATE $LD_{50}$ VALUES

SMC : Salt-marsh Caterpillar
TB : Tobacco Budworm
CL : Cabbage Looper
BBA : Black Bean Aphid
GC : German Cockroach
Toxicant: N-(Mercaptomethyl)phthalimide S-(O,O-dimethyl phosphorodithioate)
Weight ratio of activator to insecticide is 1:1 in all tests.

| | SMC | TB | CL | BBA | GC |
|---|---|---|---|---|---|
| Toxicant | 0.05 | 0.1 | 0.03 | 0.001 | 0.03 |
| Toxicant+Example 1 | >.05 | .05 | .03 | .0008 | .02 |
| Example 1 | >.05 | .1 | >.1 | >.05 | >.1 |
| Activating Factor | | 1.0 | >.8 | >1.2 | >1.2 |
| Toxicant+Example 2 | >.05 | >.1 | .005 | .008 | .03 |
| Example 2 | >.05 | >.1 | >.1 | .05 | >.1 |
| Activating Factor | | >4.6 | | 1.2 | >.8 |
| Toxicant+Example 3 | >.05 | .05 | .01 | .003 | .03 |
| Example 3 | >.05 | .1 | >.1 | >.05 | >.1 |
| Activating Factor | | 1.0 | >2.3 | >.3 | >.8 |
| Toxicant+Example 4 | >.05 | .05 | .01 | .001 | .03 |
| Example 4 | >.05 | >.1 | .1 | >.05 | >.1 |
| Activating Factor | | >1.0 | 2.3 | >1.0 | >.8 |
| Toxicant+Example 5 | .05 | .03 | .03 | .001 | .04 |
| Example 5 | >.05 | >.1 | >.1 | >.05 | .1 |
| Activating Factor | >.05 | >1.7 | >.8 | >1.0 | .6 |
| Toxicant+Example 6 | >.05 | .01 | .01 | .0008 | .005 |
| Example 6 | >.05 | .1 | >.1 | >.05 | >.1 |
| Activating Factor | | 5.0 | >2.3 | >1.2 | >4.6 |
| Toxicant+Example 7 | .05 | .03 | .01 | .0008 | .03 |
| Example 7 | >.05 | >.1 | .1 | >.05 | >.1 |
| Activating Factor | >.5 | >1.7 | 2.3 | >1.2 | >.8 |
| Toxicant+Example 8 | >.05 | .008 | .01 | .0005 | .04 |
| Example 8 | >.05 | >.1 | <.1 | >.05 | .1 |
| Activating Factor | | >6.3 | <2.3 | >2.0 | .6 |
| Toxicant+Example 9 | >.05 | .03 | .01 | .0005 | .03 |
| Example 9 | >.05 | .1 | .1 | .05 | <.1 |
| Activating Factor | | 1.7 | 2.3 | 2.0 | <.8 |
| Toxicant+Example 10 | .008 | .01 | .01 | .0003 | .03 |
| Example 10 | .03 | >.1 | .09 | .05 | >.1 |
| Activating Factor | 2.3 | >5.0 | 2.3 | 3.3 | >.8 |
| Toxicant+Example 11 | .01 | .03 | .003 | .0003 | .008 |
| Example 11 | .05 | .05 | .03 | .05 | >.1 |
| Activating Factor | 2.5 | 1.1 | 5.0 | 3.3 | >2.9 |
| Toxicant+Example 12 | .03 | .05 | .03 | .0008 | .03 |
| Example 12 | >.05 | >.1 | .1 | >.05 | >.1 |
| Activating Factor | >.8 | >1.0 | 0.8 | >1.2 | >.8 |
| Toxicant+Example 13 | .05 | >.1 | .005 | .0008 | .03 |
| Example 13 | >.05 | >.1 | .1 | >.05 | >.1 |
| Activating Factor | >.5 | | 4.6 | >1.2 | >.8 |
| Toxicant+Example 14 | .03 | .03 | .008 | .0003 | .03 |
| Example 14 | >.05 | .1 | >.1 | >.05 | >.1 |
| Activating Factor | >.8 | 1.7 | >2.9 | >3.3 | >.8 |
| Toxicant+Example 15 | >.05 | .08 | .008 | .0005 | .01 |
| Example 15 | >.05 | >.1 | >.1 | >.05 | >.1 |
| Activating Factor | | >0.6 | >2.9 | >2.0 | >2.3 |
| Toxicant+Example 16 | >.05 | .03 | .03 | .0008 | .01 |
| Example 16 | >.05 | >.1 | >.1 | .05 | >.1 |
| Activating Factor | | >1.7 | >.8 | 1.2 | >2.3 |
| Toxicant+Example 17 | .03 | .03 | .005 | .0008 | .02 |
| Example 17 | .05 | >.1 | .03 | .05 | >.1 |
| Activating Factor | .8 | >1.7 | 3.0 | 1.2 | >1.2 |
| Toxicant+Example 18 | .01 | .03 | .01 | .0003 | .009 |

TABLE II-continued

CONTACT ACTIVITY: APPROXIMATE LD$_{50}$ VALUES

SMC : Salt-marsh Caterpillar
TB : Tobacco Budworm
CL : Cabbage Looper
BBA : Black Bean Aphid
GC : German Cockroach
Toxicant: N-(Mercaptomethyl)phthalimide S-(O,O-dimethyl phosphorodithioate)
Weight ratio of activator to insecticide is 1:1 in all tests.

|  | SMC | TB | CL | BBA | GC |
|---|---|---|---|---|---|
| Example 18 | .05 | <.1 | .1 | >.05 | >.1 |
| Activating Factor | 2.5 | <1.7 | 2.3 | >3.3 | >2.6 |

The compositions of this invention are generally embodied in forms suitable for convenient application. For example, the compositions can be incorporated into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed either as the sole pesticide component or in admixture with other compounds having similar utility. The pesticide formulations of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compositions can be applied directly to feedstuffs, seeds, etc., upon which the pests feed. When applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the preparation is ingested or penetrates into the body of the pest.

The precise manner in which the pesticidal compositions of this invention are used in any particular instance will be readily apparent to a person skilled in the art. Generally, the active pesticidal composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

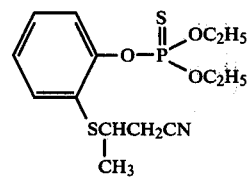

What is claimed is:

1. A compound having the formula